United States Patent [19]
Bacha et al.

[11] 4,137,419
[45] Jan. 30, 1979

[54] PROCESS FOR PREPARING 4-NITRO-O-PHTHALIC ACID

[75] Inventors: John D. Bacha; Anatoli Onopchenko, both of Monroeville; Johann G. D. Schulz, Pittsburgh, all of Pa.

[73] Assignee: Gulf Research & Development Company, Pittsburgh, Pa.

[21] Appl. No.: 814,213

[22] Filed: Jul. 11, 1977

[51] Int. Cl.$^2$ ............................................. C07C 51/24
[52] U.S. Cl. .................................................... 562/408
[58] Field of Search ........................ 260/524 N, 523 R

[56] References Cited
U.S. PATENT DOCUMENTS

| 3,978,117 | 8/1976 | Bacha | 260/523 R |
| 3,978,118 | 8/1976 | Onopchenko | 260/523 R |
| 3,978,119 | 8/1976 | Onopchenko | 260/523 R |

Primary Examiner—A. Siegel

[57] ABSTRACT

A process for converting (1) an indene, (2) a polyindene, (3) a dihydronaphthalene or (4) a polydihydronaphthalene to 4-nitro-o-phthalic acid which involves nitrating said indene, polyindene, dihydronaphthalene or polydihydronaphthalene and then oxidizing said nitrated indene, polyindene, dihydronaphthalene or polydihydronaphthalene with nitric acid.

13 Claims, No Drawings

PROCESS FOR PREPARING 4-NITRO-O-PHTHALIC ACID

BACKGROUND OF THE INVENTION

1. Field of the Invention

This invention relates to a process for converting (1) an indene, (2) a polyindene, (3) a dihydronaphthalene or (4) a polydihydronaphthalene to 4-nitro-o-phthalic acid which comprises nitrating said indene, polyindene, dihydronaphthalene or polydihydronaphthalene and then oxidizing said nitrated indene, polyindene, dihydronaphthalene or polydihydronaphthalene with nitric acid.

2. Description of Prior Art

A logical procedure for preparing 4-nitro-o-phthalic acid would appear to involve the nitration of phthalimide to give 4-nitrophthalimide and hydrolyzing the latter. The synthesis is costly, however, because of the low yields of 4-nitro-o-phthalic acid obtained (50 to 52 per cent) and the cost of the phthalimide [Organic Synthesis, Col. Volume II, John Wiley and Sons, New York, 1943, pages 457 to 459].

If, on the other hand, phthalic acid or phthalic anhydride is nitrated, an approximately 50/50 mixture of 4-nitro-o-phthalic and 3-nitro-o-phthalic acids is obtained. This reaction is a known procedure for the synthesis of 3-nitro-o-phthalic acid, despite the low yields (28 to 31 per cent) of 3-nitro-o-phthalic acid obtained. [Organic Syntheses, Col. Volume I, John Wiley and Sons, New York, 1932, pages 408 to 412]. In preparing 3-nitro-o-phthalic acid by this method, advantage is taken of the lower water solubility of 3-nitro-o-phthalic acid. The latter material is then recovered by crystallization from water. 4-Nitro-o-phthalic acid can be obtained from washings and other liquors after separation of 3-nitro-o-phthalic acid via evaportion, esterification, separation of isomeric esters and subsequent hydrolysis of the separated ester of 4-nitro-o-phthalic acid. This procedure would be expected to be laborious, costly and to result in low yields of 4-nitro-o-phthalic acid.

SUMMARY OF THE INVENTION

We have found that we can obtain 4-nitro-o-phthalic acid in extremely high yields by a process which involves nitrating an organic compound selected from the group consisting of (1) an indene, (2) a polyindene, (3) a dihydronaphthalene and (4) a polydihydronaphthalene and then oxidizing said nitrated indene, polyindene, dihydronaphthalene or polydihydronaphthalene with nitric acid.

DESCRIPTION OF THE PROCESS

The indene that can be converted to 4-nitro-o-phthalic acid by the process defined and claimed herein can be defined as follows:

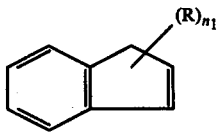

wherein R is an alkyl radical having from one to three carbon atoms, such as methyl, ethyl and propyl, and $n_1$ is an integer from zero to 2, preferably 0.

The polyindene used herein can be defined as follows:

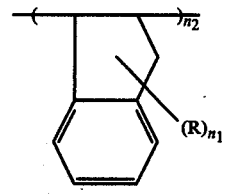

wherein R and $n_1$ can be as defined above and $n_2$ is an integer from 2 to about 100, generally from about 3 to about 50.

The dihydronaphthalene charge that can also be used herein can be defined as follows:

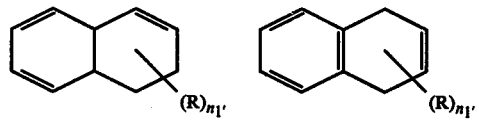

or a mixture of the two, wherein R and $n_1$ can be as defined above.

The polydihyronaphthalene charge suitable for use herein can be defined as follows:

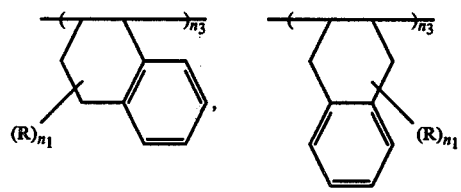

or mixtures of the two, or copolymers of the two isomeric dihydronaphthalenes

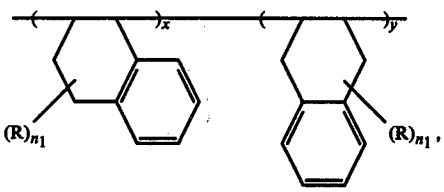

wherein the monomeric components are arranged in random order, $x + y = n_3$, and R and $n_1$ can be as defined above and $n_3$ is an integer from 2 to about 100, generally from about 3 to about 50.

Specific examples of each of the above charges include the following: indene; 1-methylindene; 2-methylindene; 3-methylindene; 3-ethylindene; 3-propylindene; 3,3-dimethylindene; 3-methyl-3-ethylindene; 1,2-dihydronaphthalene; 1-methyl-1,2-dihydronaphthalene; 2-methyl-1,2-dihydronaphthalene; 3-methyl-1,2-dihydronaphthalene; 4-methyl-1,2-dihydronaphthalene; 3-ethyl-1,2-dihydronaphthalene; 4-ethyl-1,2-dihydronaphthalene; 3-propyl-1,2-dihydronaphthalene; 3,3-dimethyl-1,2-dihydronaphthalene; 3,4-dimethyl-1,2-dihydronaphthalene; 4,4-dimethyl-1,2-dihydronaphthalene; 1,4-dihydronaphthalene; 1-methyl-1,4-dihydronaphthalene; 2-methyl-1,4-dihydronaphthalene; 1-ethyl-1,4-dihydronaphthalene; 1-propyl-1,4-dihydronaphthalene; 1,1-dimethyl-1,4-dihydronaphthalene, etc.

The indene polymers and the dihydronaphthalene polymers defined as suitable charges herein can be obtained by any suitable or convenient procedure known in the art.

Thus, indene is readily polymerized in the presence of an acid catalyst [B.Golding, "Polymers and Resins", D. Van Nostrand Co., Inc., page 35] or by using Friedel-Crafts type catalyst [British Pat. No. 950,602[; methyl indenes are polymerized by the action of alkyl and aryl sulfates at 0°–70° C. [U.S. Pat. No. 2,437,278]; dihydronaphthalenes are polymerized by the action of sodium naphthalene [N. D. Scott and J. F. Walker, Ind. Eng. Chem. 32, 312–315 (1940)] or with BuLi [U.S.S.R. 171,559, May 1965] or with $TiCl_4$ [U.S.S.R. 134,022] as catalysts.

The nitration of each of the above charges can be effected by bringing the same into contact with concentrated aqueous nitric acid under specific conditions defined hereinafter. This can be done, for example, by introducing the charge into nitric acid, by introducing the nitric acid into the charge or by bringing the charge and the nitric acid into simultaneous contact with each other. The latter procedure is preferred, since the molar ratio of the charge and nitric acid can be maintained substantially constant throughout the reaction. The aqueous nitric acid used will have a concentration of about 70 to about 95 weight per cent, preferably about 85 to about 95 weight per cent. The amount of nitric acid needed is that amount at least sufficient to place one nitro group on each of the aromatic nuclei. The molar ratios of nitric acid, as 100 per cent nitric acid, relative to indene, dihydronaphthalene or to each monomeric member of the respective polymers, will be in the range of about 3:1 to about 30:1, preferably about 3:1 to about 20:1. The temperature during nitration can vary over a wide range, for example, from about −40° to about 90° C., preferably from about −10° to about 50° C. Pressure does not affect the course of the reaction and pressures up to about 100 pounds per square inch gauge (about seven kilograms per square centimeter), or even higher, can be used, but, in general ambient pressure is sufficient. The time required for nitration can vary over a wide range, for example, from about one minute to about eight hours, but in general a period of about 10 minutes to about four hours is sufficient. During the reaction the reaction mixture is stirred by any suitable means.

During nitration a solvent can be present, for example, as a temperature moderator or to help maintain the reaction system homogeneous by dissolving intermediates, etc. Examples of such solvents are sulfuric acid, acetic anhydride, methylene chloride, etc. If used, the molar ratio of nitric acid, as 100 per cent nitric acid, to said solvent, can be in the range of about 1:0 to about 1:20, preferably about 1:0 to about 1:10. If the solvent is used it can be added to the reaction system at any time, but preferably it is added together with the organic component, for example, indene.

At the end of the nitration period, the nitrated compounds obtained are subjected to oxidation to obtain the desired 4-nitro-o-phthalic acid. This can be done in one of two ways. The nitrated organic compounds can be separated from the total reaction mixture and the nitrated organic compounds alone can be subjected to oxidation or the total reaction product at the end of the nitration period can be subjected to oxidation.

To effect separation and recovery of the nitrated compounds, the total reaction product is diluted with water to stop the nitration reaction. The amount of water added is that amount sufficient to reduce the concentration of the nitric acid in the range of about one to about 50 weight per cent, preferably about 15 to about 40 weight per cent, while maintianing the temperature of the resulting mixture in the range of about 0° to about 50° C., preferably in the range of about 0° to about 30° C. As a result of such action, the desired nitrated organic compounds precipitate out of solution and can be recovered in any suitable manner, for example by filtration. The solids thus obtained can be washed with water, if desired, to remove water-soluble components in admixture therewith.

If the total nitrated reaction product is to be subjected to oxidation, total nitrated reaction product is merely diluted with water, as above, sufficient to obtain a final nitric acid concentration of about five to about 50 weight per cent, preferably about 10 to about 40 weight per cent.

The oxidation stage is easily effected. The total reaction product, after dilution, as defined above, or the recovered nitrated product, together with aqueous nitric acid having a concentration of about five to about 50 weight per cent, preferably about 10 to about 40 weight per cent, is heated, while stirring, for example, in a temperature range of about 135° to about 210° C., preferably about 155° to about 190° C., and a pressure of about 150 to about 500 pounds per square inch gauge (about 10.5 to about 35.2 kilograms per square centimeter), preferably about 200 to about 350 pounds per square inch gauge (about 14.1 to about 24.6 kilograms per square centimeter), for about 0.1 to about 10 hours, preferably about one to about four hours. The mol ratio of nitric acid, as 100 per cent acid, relative to indene, dihydronaphthalene or to each monomeric member of the respective polymers in the original charge, will be in the range of about 5:1 to about 25:1 preferably about 5:1 to about 15:1. Conversion of nitrated product to oxidation products can be as high as about 100 per cent.

Recovery of the desired 4-nitro-o-phthalic acid from the resulting oxidation product can be effected in any conventional manner. For example, the reaction product can be cooled to a temperature in the range of about 20° to about 40° C., and depressured to ambient pressure, as a result of which volatiles, such as water, carbon dioxide, and nitrogen oxides will be removed. Remaining water and nitric acid can be removed from the remaining product by stripping, under a reduced pressure, for example, at about 20 to about 100 millimeters of mercury in a temperature range of about 25° to about 75° C. If desired, occluded water-soluble contaminants such as nitric acid that may still be present in the solid 4-nitro-o-phthalic acid product can be removed from said product by slurrying with water and subjecting the resulting product to evaporation to remove water and contaminant.

The product recovered will generally possess the following components in the following amounts:

| Compound | Mol Per Cent | |
|---|---|---|
| | Broad Range | General Range |
| 4-nitro-o-phthalic acid | 65–90 | 80–90 |
| 3-nitro-o-phthlatic acid | 1–6 | 2–3 |
| phthalic acid | 0–4 | 0.1–1 |
| unidentified materials | 0–34 | 6–18 |

From the above it can be seen that the molar ratio of the desired 4-nitro-o-phthalic acid to 3-nitro-o-phthalic acid is in the range of about 10:1 to about 90:1, generally about 27:1 to about 45:1.

The fact the only essential isomer obtained herein is the 4-nitro-o-phthalic acid rather than the 3-isomer is totally unexpected. For example, if one were to nitrate an indene and/or dihydronaphthalene, it would be expected that nitration would be random on the aromatic nucleus and oxidation of the nitrated intermediate would lead to substantially equivalent amounts of the 3- and 4-nitro isomers of phthalic acid by analogy with the nitration of indane and tetrahydronaphthalene, wherein nitration on the aromatic ring is random (JACS, 87 4794, 1965).

If desired higher purity of the 4-isomer from the oxidation product defined above can be effected by recrystallization from diethyl ether, as shown, for example in Organic Synthesis, Collective Volume II, John Wiley & Sons, New York, 1943, pages 457–458.

The 4-nitro-o-phthalic acid obtained herein can be utilized in numerous ways. For example, it can be converted to the corresponding anhydride by following the procedure defined in U.S. Pat. No. 3,979,416, dated Sept. 7, 1976 to D'Alelio et al., which, in turn, can be reacted with KF to form 4-fluorophthalic anhydride suitable for preparing polymers by following the procedure in U.S. Pat. No. 3,956,321, dated May 11, 1976, to Markezich. If desired the 4-nitro-o-phthalic acid can be converted to 4-amino-o-phthalic acid and to polymers following the procedure of U.S. Pat. No. 3,940,322, dated Feb. 24, 1976, to Phillips et al.

DESCRIPTION OF PREFERRED EMBODIMENTS

A number of runs were carried out wherein indene was nitrated with concentrated nitric acid and isolated nitroindenes were subsequently oxidized with dilute nitric acid. The indene employed was composed of a mixture of 91 weight per cent indene, six weight per cent indane and three weight per cent other unidentified hydrocarbons of similar volatility. Indene was added slowly, with stirring, to concentrated nitric acid at a selected temperature level. Upon completion of the addition, stirring was continued for 0.5 hour. The product mixture was poured onto ice and the resulting mixture was diluted further with water. The nitroindenes, which precipitated as tan granular solids, were separated by vacuum filtration, washed with water and air dried. Nitric acid consumed was determined by titration of aliquots of the filtrate and washings with a standard base. In the oxidation step, the nitroindenes so obtained were combined with dilute nitric acid in a one-liter, stainless steel autoclave, the autoclave pressured with about 50 pounds per square inch gauge (3.5 kilograms per square centimeter) of nitrogen and the mixture heated, with stirring, to the desired temperature over a period of about one hour. Heating and stirring at a selected temperature level was continued for a selected period of time. Maximum pressure during oxidation was controlled by an automatic relief device. After cooling the system to ambient temperature over a period of 0.5 hour, pressure was released, the system flushed with nitrogen and the product mixture, an aqueous solution containing a very small amount of suspended insoluble material, was siphoned from the autoclave. The insolubles were separated by vacuum filtration and the product isolated from the clarified product solution as a non-volatile residue by vacuum rotary evaporation. The original residue was thrice combined with water (200 milliliters) and reevaporated to complete removal of excess nitric acid. Nitric acid consumed in the oxidation step was determined by titration of aliquots of the evaporation liquids with standard base. The composition of the product was determined by gas chromatographic analysis of an acetone solution of a sample of the product using a 6-feet by ⅛-inch stainless steel column packed with 10 per cent OV-1 on 80/100 mesh Gas Chrom Q and operated isothermally at 175° C. A standard solution of a mixture of 4-nitro-o-phthalic acid and 3-nitro-o-phthalic acid in acetone was used as a reference. Under conditions of analysis, nitrophthalic acids and phthalic acids dehydrate. Peaks produced by the corresponding anhydrides appeared on the chromatograms. The data obtained are summarized below in Table I.

TABLE I

| Run No. | 1 | 2 | 3 | 4 |
|---|---|---|---|---|
| Nitration[a] | | | | |
| $HNO_3$ Concentration, Weight Per Cent | 90 | 90 | 90 | 70 |
| $HNO_3$[b]: Grams (mols) | 162.5 (2.579) | 162.5 (2.579) | 162.5 (2.579) | 164.0 (2.603) |
| Indene: Grams (mols[c]) | 30 (0.258) | 30 (0.258) | 30 (0.258) | 30 (0.258) |
| Time, Hours[d] | 4.5 | 3.3 | 3.5 | 3.5 |
| Temperature, °C. | −6±2 | 10±2 | 25±3 | 25±3 |
| $HNO_3$ Consumed, Mols | 0.39 | 0.384 | 0.433 | 0.425 |
| $HNO_3$ Consumed, Mol Per Mol of Indene | 1.51 | 1.488 | 1.678 | 1.65 |
| Product: Grams (Per Cent[e]) | 44.8 (94.1) | 47.1 (99.8) | 46.8 (94.7) | 34.6 (70.5) |
| Oxidation | | | | |
| Nitroindenes (NI): Grams (Mols[e]) | 30 (0.154) | 45 (0.246) | 45 (0.235) | 34.2 (0.180) |
| $HNO_3$ Concentration, Weight Per Cent | 25 | 25 | 25 | 25 |
| $HNO_3$[b]: Grams (Mols) | 94.8 (1.50) | 125.2 (1.988) | 125.2 (1.988) | 113.5 (1.80) |
| Mols $HNO_3$ Per Mols NI | 9.7 | 8.1 | 8.5 | 10 |
| Time, Hours | 1.0 | 1.0 | 1.0 | 1.5 |
| Temperature, °C. | 180±1 | 183±1 | 186±1 | 184±1 |
| Pressure, Pounds Per Square Inch Gauge (Kilograms Per Square Centimeter) | 250 (17.6) | 275 (19.3) | 275 (19.3) | 250 (17.6) |
| $HNO_3$ Consumed, Mols | 0.82 | 1.114 | 1.013 | 0.562 |
| $HNO_3$ Consumed Per Mol NI | 5.32 | 4.53 | 4.31 | 3.13 |
| Product: Grams (Per Cent[e] [f]) | 33.1 (101.8) | 48.2 (92.9) | 46.5 (93.8) | 32.7 (86.1) |
| Analysis[g], Per Cent 4/3/P/O | 93.0/2.8/0.7/3.5 | 91.1/2.9/0.9/7.1 | 86.9/3.0/0.9/9.2 | 32.5/2.8/58.6/6.1 |

[a] At atmospheric pressure
[b] As 100 per cent $HNO_3$
[c] Assuming 100 per cent
[d] Includes 0.5 hour post addition stirring period
[e] Calculated assuming all $HNO_3$ consumed goes to form mono- or dinitroindenes
[f] Weight per cent, calculated versus maximum mols of 4-nitro-o-phthalic acid possible using assumed molecular weight of nitroindenes charged
[g] Mol per cent 4-nitro-o-phthalic acid/3-nitro-o-phthalic acid/phthalic acid/other (unknowns) by GLC.

A number of runs were carried out using indene of the same composition as above wherein indene was nitrated with concentrated nitric acid and the nitroindenes produced were subsequently oxidized without isolation. The total nitrated product was diluted with water to obtain a desired nitric acid concentration therein and this mixture was subjected to oxidation under selected conditions. Thus, excess nitric acid present in the nitration was used as oxidant in the second stage. More specifically, indene was added slowly, with stirring, to concentrated nitric acid while maintaining a selected temperature level. Stirring was continued for 0.5 hour after completion of the addition. The product mixture was poured onto a weighted amount of ice and the resulting mixture further diluted with a measured amount of water. This mixture was charged to the autoclave for oxidation along with enough water to achieve the desired nitric acid concentration. The amount of dilution water added to the nitration product was calculated knowing how much nitric acid was consumed in the nitration step from earlier, parallel runs wherein nitroindenes were isolated. Oxidation, oxidation product recovery and product isolation proceeded as in Runs Nos. 1 to 4. The total amount of nitric acid consumed in the nitration and oxidation steps was determined by titration of aliquots of evaporation liquids with standard base. Nitric acid consumed in the nitration step was assumed to be equal to that consumed in earlier, parallel runs wherein nitroindenes were isolated. Nitric acid consumed in the oxidation stage was determined by difference. The data obtained are summarized below in Table II.

TABLE II

| Run No. | 5 | 6 | 7 | 8 | 9 | 10 |
|---|---|---|---|---|---|---|
| Nitration$^{(a,b)}$ | | | | | | |
| Indene, Grams (Mols$^{(c)}$) | 30 (0.258) | 30 (0.258) | 30 (0.258) | 30 (0.258) | 30 (0.258) | 30 (0.258) |
| Mols HNO$_3$ Per Mol of Indene | 10 | 10 | 10 | 10 | 10 | 10 |
| Time, Hours$^{(d)}$ | 3.2 | 3.3 | 3.2 | 3.5 | 3.4 | 3.3 |
| Temperature, ° C. | −10±2 | −10±2 | −10±2 | 10±2 | 10±2 | 10±2 |
| HNO$_3$ Consumed, Mols | 0.387 | 0.387 | 0.387 | 0.400 | 0.400 | 0.400 |
| HNO$_3$ Consumed, Mol Per Mol of Indene | 1.5 | 1.5 | 1.5 | 1.55 | 1.55 | 1.55 |
| Product: Grams (Per Cent$^{(e)}$) | 47.4 (100) | 47.4 (100) | 47.4 (100) | 48.0 (100) | 48.0 (100) | 48.0 (100) |
| Oxidation | | | | | | |
| Nitroindenes (NI) Grams (Mols) | 47.4 (0.258) | 47.4 (0.258) | 47.4 (0.258) | 48.0 (0.258) | 48.0 (0.258) | 48.0 (0.258) |
| HNO$_3$ Concentration, Weight Per Cent | 25 | 25 | 25 | 25 | 25 | 25 |
| HNO$_3$$^{(f)}$: Grams (Mols) | 138.1 (2.192) | 138.1 (2.192) | 138.1 (2.192) | 137.3 (2.179) | 137.3 (2.179) | 137.3 (2.179) |
| Mol HNO$_3$ Per Mol NI | 8.5 | 8.5 | 8.5 | 8.4 | 8.4 | 8.4 |
| Time, Hours; Temperature, ° C. | 2.0;166±1 | 1.0;175±1 | 1.0; 185±1 | 1.0; 165±1 | 2.0; 166±1 | 1.0; 175±1 |
| Pressure, Pounds Per Sqaure Inch Gauge (Kilograms Per Square Centimeter) | 255 (17.9) | 265 (18.6) | 260 (18.3) | 250 (17.6) | 250 (17.6) | 250 (17.6) |
| HNO$_3$ Consumed, Mols | 1.155 | 1.116 | 1.340 | 1.044 | 1.172 | 1.122 |
| HNO$_3$ Consumed, Mols Per Mol NI | 4.48 | 4.43 | 5.19 | 4.05 | 4.54 | 4.35 |
| Aqueous Acid Insolubles, Grams | 0.6 | 0.9 | 0.5 | 2.8 | 0.5 | 0.6 |
| Product, Grams, (Per Cent$^{(g)}$) | 52.8 (96.9) | 51.1 (93.8) | 55.9 (102.5) | 49.2 (90.3) | 51.8 (95.0) | 52.5 (96.3) |
| Analysis$^{(h)}$: Per Cent 4/3/P/O | 82.9/2.1/ 0.5/14.5 | 84.6/2.5/ 0.5/12.4 | 86.0/2.3/ 1.2/10.5 | 84.9/2.0/ 0.7/12.4 | 89.2/2.8/ 0.6/7.4 | 85.2/2.3/ 0.6/11.9 |
| Nitration and Oxidation | | | | | | |
| HNO$_3$ Consumed, Mols | 1.542 | 1.503 | 1.727 | 1.444 | 1.572 | 1.522 |
| HNO$_3$ Consumed, Mols Per Mol of Indene | 5.98 | 5.83 | 6.69 | 5.60 | 6.09 | 5.90 |

| Run No. | 11 | 12 | 13 | 14 | 15 | 16 |
|---|---|---|---|---|---|---|
| Nitration$^{(a,b)}$ | | | | | | |
| Indene, Grams (Mols$^{(c)}$) | 30 (0.258) | 37.5 (0.323) | 30 (0.258) | 25 (0.215) | 37.5 (0.323) | 30 (0.258) |
| Mols HNO$_3$ Per Mol of Indene | 10 | 8 | 10 | 12 | 8 | 10 |
| Time, Hours$^{(d)}$ | 3.5 | 3.0 | 3.2 | 3.4 | 3.4 | 3.2 |
| Temperature, ° C. | 10±2 | 25±4 | 25±5 | 25±5 | 26±3 | 26±3 |
| HNO$_3$ Consumed, Mols | 0.400 | 0.533 | 0.426 | 0.355 | 0.533 | 0.426 |
| HNO$_3$ Consumed, Mol Per Mol of Indene | 1.55 | 1.65 | 1.65 | 1.65 | 1.65 | 1.65 |
| Product: Grams (Per Cent$^{(e)}$) | 48.0 (100) | 61.5 (100) | 49.1 (100) | 40.9 (100) | 61.5 (100) | 49.1 (100) |
| Oxidation | | | | | | |
| Nitroindenes (NI) Grams (Mols) | 48.0 (0.258) | 61.5 (0.323) | 49.1 (0.258) | 49.9 (0.215) | 61.5 (0.323) | 49.1 (0.258) |
| HNO$_3$ Concentration, Weight Per Cent | 25 | 25 | 25 | 25 | 25 | 25 |
| HNO$_3$$^{(f)}$: Grams (Mols) | 137.3 (2.179) | 128.9 (2.046) | 135.6 (2.153) | 140.1 (2.224) | 128.9 (2.046) | 135.6 (2.153) |
| Mol HNO$_3$ Per Mol NI | 8.4 | 6.3 | 8.3 | 10.3 | 6.3 | 8.3 |
| Time, Hours; Temperature, ° C. | 1.0; 185±1 | 1.0; 185±1 | 1.0; 185±1 | 1.0; 184±1 | 2.0; 184±1 | 2.0; 184±1 |
| Pressure, Pounds Per Square Inch Gauge (Kilograms Per Square Centimeter) | 255 (17.9) | 250 (17.6) | 250 (17.6) | 250 (17.6) | 255 (17.9) | 250 (17.6) |
| HNO$_3$ Consumed, Mols | 1.295 | 1.524 | 1.308 | 1.181 | 1.502 | 1.246 |
| HNO$_3$ Consumed, Mols Per Mol NI | 5.02 | 4.72 | 5.07 | 5.49 | 4.65 | 4.83 |
| Aqueous Acid Insolubles, Grams | 0.3 | n.d.$^{(i)}$ | n.d. | n.d. | n.d. | n.d. |
| Product, Grams, (Per Cent$^{(g)}$) | 51.1 (93.8) | 62.7 (92.1) | 50.3 (92.3) | 43.4 (95.6) | 68.1 (89.0) | 54.5 (92.5) |
| Analysis$^{(h)}$: Per Cent 4/3/P/O | 82.9/2.5/ 0.5/14.1 | 83.2/2.9/ 1.8/12.1 | 84.0/2.6/ 0.9/12.5 | 80.9/2.7/ 0.6/15.8 | 81.7/3.0/ 1.7/13.6 | 76.8/3.6/ 1.6/18.0 |
| Nitration and Oxidation | | | | | | |
| HNO$_3$ Consumed, Mols | 1.695 | 2.057 | 1.734 | 1.536 | 2.035 | 1.671 |
| HNO$_3$ Consumed, Mols Per Mol of | | | | | | |

TABLE II-continued

| | | | | | | |
|---|---|---|---|---|---|---|
| Indene | 6.57 | 6.37 | 6.72 | 7.14 | 6.30 | 6.48 |

Underlined numbers are estimated values
[a] At atmospheric pressure
[b] Each run used 180.6 grams of 90 per cent aqueous nitric acid
[c] As 100 per cent
[d] Includes 0.5 hour post addition stirring period
[e] Calculated weight assuming all HNO$_3$ consumed goes to mono- or dinitroindenes
[f] As 100 per cent HNO$_3$
[g] Weight per cent, relative to mols indene charged
[h] Mol per cent 4-nitro-o-phthalic acid/3-nitro-o-phthalic acid/phthalic acid/other (unknowns) by GLC.
[i] Not determined.

An additional run was completed wherein nitration was carried out with a mixture of nitric acid and sulfuric acid. The same indene used above was added slowly, with stirring, to a mixture of concentrated nitric and sulfuric acids maintained at a selected temperature level. Stirring was continued for 0.5 hour after completion of the addition. The product mixture was poured onto ice. The nitroindenes were isolated from the mixture and subsequently oxidized as described above under selected conditions.

Still an additional run was carried out wherein polyindene was nitrated with concentrated nitric acid and the nitropolyindenes produced subsequently oxidized without isolation. Polyindene used was prepared by the acid-catalyzed polymerization of indene. Indene in the amount of 50 grams was added slowly, with stirring, to 85 per cent aqueous sulfuric acid (422 grams as 100 per cent sulfuric acid) over a two-hour period while maintaining a temperature of 10 ± 2° C. and the resulting mixture was stirred at 10° C. for 0.3 hour. Polyindene developed as a granular precipitate during the addition period. The product mixture was poured onto ice, and the resulting mixture was further diluted with water and the insoluble polyindenes were separated by vacuum filtration, washed with water until the washings were neutral to litmus and air dried. The dried product, amounting to 49.5 grams, was washed with hexane to remove occluded monomer, resulting in the production of 43.4 grams of purified polyindenes. The polyindenes were characterized by elemental analysis and gel permeation chromatography. Gel permeation chromatography revealed the polymer to contain a molecular weight distribution from about 230 (dimer) to about 10,000 (about 86 indene units). About 50 weight per cent of the sample contained from two to six indene units and the remainder from six to 86 units Polyindene was nitrated by adding the polymer slowly, while stirring, to concentrated nitric acid while maintaining a selected temperature level. After stirring for 0.5 hours, the product mixture was poured onto a weighed amount of ice and the resulting mixture was further diluted with a measured volume of water. This mixture was charged to the autoclave for oxidation along with enough water to achieve the desired nitric acid concentration. Oxidation, oxidation product recovery and product isolation proceeded as indicated above. The results obtained from the latter two runs are summarized below in Table III.

TABLE III

| Run No. | 17 | 18[a] |
|---|---|---|
| Nitration[b,c] | | |
| 96.5 Weight Per Cent Aqueous H$_2$S$_4$O, Grams | 184 | — |
| Indene: Grams (Mols) | 30[d] (0.258)[e] | — |
| Polyindene: Grams (Mols) | — | 30 (0.258)[f] |
| Time, Hours | 3.2 | 3.5 |
| Temperature, ° C. | 10 ± 3 | 10 ± 2 |
| HNO$_3$ Consumed, Mols | 0.457 | 0.400 |
| HNO$_3$ Consumed, Mol Per Mol of Indene | 1.77 | 1.55 |
| Product: Grams (Per Cent[g]) | 50.6 (100) | 48.0 (100) |
| Oxidation | | |
| Nitroindenes (NI): Grams (Mols) | 48 (0.245) | 48 (0.258) |
| HNO$_3$ Concentration, Weight Per Cent | 25 | 25 |
| HNO$_3$[h]: Grams (Mols) | 125.2 (1.987) | 137.3 (2.179) |
| Mol HNO$_3$ Per Mol NI | 8.1 | 8.4 |
| Time, Hours | 1.0 | 1.0 |
| Temperature, ° C. | 175 ± 1 | 175 ± 1 |
| Pressure, Pounds Per Square Inch Gauge | 260 (18.3) | 260 (18.3) |
| (Kilograms Per Square Centimeter) | | |
| HNO$_3$ Consumed, Mols | 1.231 | 1.169 |
| HNO$_3$ Consumed Mol Per Mol of NI | 5.03 | 4.53 |
| Aqueous Acid Insolubles, Grams | 0.4 | 1.0 |
| Product: Grams (Per Cent[i]) | 50.8 (98.2) | 50.4 (92.5) |
| Analysis[j]: Per Cent 4/3/P/O | 36.5/0.7/1.1/61.7 | 80.2/1.6/0.5/17.7 |
| Nitration and Oxidation | | |
| HNO$_3$ Consumed Mols | — | 1.569 |
| HNO$_3$ Consumed, Mols Per Mol of | | |

TABLE III-continued

| Run No. | 17 | 18[a] |
|---|---|---|
| Indene | 6.80 | 6.08 |

Figures underlined are estimated values
[a] Tandem nitration/oxidation - no nitroindenes isolation
[b] At ambient pressure
[c] Each run consumed 180.6 grams of 90 per aqueous HNO$_2$ = 162.5 grams, 2.579 mols HNO$_3$
[d] 91 per cent
[e] Assuming 100 per cent
[f] Indene equivalents
[g] Calculated assuming all HNO$_3$ goes to mono- or dinitroindenes
[h] As 100 per cent
[i] Weight per cent, relative to mols of indene in system
[j] Mol per cent 4-nitro-o-phthalic acid/3-nitro-o-phthalic acid/phthalic and/other (unknown) by GLC.

An additional run was carried out wherein 1,2-dihydronaphthalene was nitrated with concentrated nitric acid and the nitrodihydronaphthalenes produced subsequently oxidized without isolation. The 1,2-dihydronaphthalene employed was composed of a mixture of 97 weight per cent 1,2-dihydronaphthalene, about one weight per cent each of tetrahydronaphthalene, 1,4-dihydronaphthalene and naphthalene, and traces of other unidentified hydrocarbons of similar volatility. Nitration, oxidation, oxidation product recovery and product isolation wre carried out substantially the same as in Run No. 10 described above. The results obtained are summarized below in Table IV.

TABLE IV

| Run No. | 19[a] |
|---|---|
| Nitration[b] | |
| Dihydronaphthalene, Grams (Mols[c]) | 30 (0.230) |
| Mols HNO$_3$ Per Mol of Dihydronaphthalene | 11.2 |
| Time, Hours[d] | 3.3 |
| Temperature, °C. | 10 ± 3 |
| HNO$_3$ Consumed, Mols | 0.3565 |
| HNO$_3$ Consumed, Mol Per Mol of Dihydronaphthalene | 1.55 |
| Product: Grams (Per Cent[e]) | 46.0 (100) |
| Oxidation | |
| Nitrodihydronaphthalenes (NDN), Grams (Mols) | 46.0 (0.230) |
| HNO$_3$ Concentration, Weight Per Cent | 25.7 |
| HNO$_3$[f]: Grams (Mols) | 140.0 (2.222) |
| Mol HNO$_3$ Per Mol NDN | 9.7 |
| Time, Hours | 1.0 |
| Temperature, °C. | 175 ± 1 |
| Pressure, Pounds Per Square Inch Gauge (Kilograms Per Square Centimeter) | 265 (18.6) |
| HNO$_3$ Consumed, Mols | 1.192 |
| HNO$_3$ Consumed, Mols Per Mol NDN | 5.18 |
| Aqueous Acid Insolubles, Grams | 0.7 |
| Product, Grams (Per Cent[g]) | 41.7 (86.0) |
| Analysis[h]: Per Cent 4/3/P/O | 68.4/6.0/3.5/22.1 |
| Nitration and Oxidation | |
| HNO$_3$ Consumed, Mols | 1.548 |
| HNO$_3$ Consumed, Mols Per Mol of Dihydronaphthalene | 6.73 |

Underlined numbers are estimated values
[a] Tandem nitration/oxidation - no dihydronaphthalenes isolation
[b] Used 180.6 grams of 90 per cent nitric acid = 162.5 grams, 0.2579 mols HNO$_3$
[c] As 100 per cent
[d] Includes 0.5 hour post addition stirring period
[e] Calculated weight assuming all HNO$_3$ consumed goes to mono- or dinitrodihydronaphthalenes
[f] As 100 per cent HNO$_3$
[g] Weight per cent, relative to mols dihydronaphthalene charged
[h] Mol per cent 4-nitro-o-phthalic acid/3-nitro-o-phthalic acid/phthalic acid/other (unknowns) by GLC.

Obviously, many modifications and varitions of the invention, as hereinabove set forth, can be made without departing from the spirit and scope thereof, and therefore only such limitations should be imposed as are indicated in the appended claims.

We claim:

1. A process for converting an organic compound selected from the group consisting of (1) an indene, (2) a polyindene, (3) a dihydronaphthalene and (4) a polydihydronaphthalene to 4-nitro-o-phthalic acid which comprises nitrating said organic compound with concentrated nitric acid and then oxidizing said nitrated organic compound with dilute nitric acid, said nitration being conducted with an aqueous nitric acid solution having a concentration of about 70 to about 95 weight per cent at a temperature of about −40° to about 90° C. over a period of about one minute to about eight hours and said oxidation being conducted with an aqueous nitric acid solution having a concentration of about five to about 50 weight per cent at a temperature of about 135° to about 210° C. for about 0.1 to about 10 hours.

2. The process of claim 1 wherein said organic compound is indene.

3. The process of claim 1 wherein said organic compound is a polyindene.

4. The process of claim 1 wherein said organic compound is dihydronaphthalene.

5. The process of claim 1 wherein said organic compound is a polydihydronaphthalene.

6. The process of claim 1 wherein said nitration is carried out with nitric acid having a concentraton of about 85 to about 95 per cent at a temperature of about −10° to about 50° C. for about ten minutes to about four hours.

7. The process of claim 1 wherein said oxidation is carried out with nitric acid having a concentration of about 10 to about 40 per cent at a temperature of about 155° to about 190° C. for about one to about four hours.

8. The process of claim 1 wherein said nitrated organic compounds are separated from the nitrated reaction mixture prior to oxidation.

9. The process of claim 1 wherein the total nitrated reaction product is subjected to oxidation.

10. The process of claim 1 wherein a solvent is also present in the reaction mixture during nitration.

11. The process of claim 10 wherein said solvent is sulfuric acid.

12. The process of claim 1 wherein the product obtained has the following composition:

| Compound | Mol Per Cent |
|---|---|
| 4-nitro-o-phthalic acid | 65-90 |
| 3-nitro-o-phthalic acid | 1-6 |
| phthalic acid | 0-4 |
| unidentified materials | 0-34 |

13. The process of claim 1 wherein the product obtained has following composition:

| Compound | Mol Per Cent |
|---|---|
| 4-nitro-o-phthalic acid | 80-90 |
| 3-nitro-o-phthalic acid | 2-3 |
| phthalic acid | 0.1-1 |
| unidentified materials | 6-18 |

* * * * *